(12) United States Patent
Mou et al.

(10) Patent No.: US 11,125,224 B2
(45) Date of Patent: Sep. 21, 2021

(54) ACTUATING AND SENSING MODULE

(71) Applicant: Microjet Technology Co., Ltd., Hsinchu (TW)

(72) Inventors: Hao-Jan Mou, Hsinchu (TW); Shih-Chang Chen, Hsinchu (TW); Jia-Yu Liao, Hsinchu (TW); Shou-Hung Chen, Hsinchu (TW); Hung-Hsin Liao, Hsinchu (TW); Chiu-Lin Lee, Hsinchu (TW); Mei-Yen Chen, Hsinchu (TW); Chi-Feng Huang, Hsinchu (TW); Yung-Lung Han, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 142 days.

(21) Appl. No.: 16/042,629

(22) Filed: Jul. 23, 2018

(65) Prior Publication Data
US 2019/0063421 A1  Feb. 28, 2019

(30) Foreign Application Priority Data
Aug. 31, 2017 (TW) .................................. 106129651

(51) Int. Cl.
*F04B 45/047* (2006.01)
*G01N 33/00* (2006.01)
(Continued)

(52) U.S. Cl.
CPC .......... *F04B 45/047* (2013.01); *B81B 3/0021* (2013.01); *G01N 1/2273* (2013.01);
(Continued)

(58) Field of Classification Search
CPC ................ F04B 45/047; G01N 1/2273; G01N 33/0009; B81B 3/0021; B81B 2201/036;
(Continued)

(56) References Cited

U.S. PATENT DOCUMENTS 6,165,347 A    12/2000 Warburton
7,284,966 B2 * 10/2007 Xu .................... F04B 19/006
                                                 417/395
(Continued)

FOREIGN PATENT DOCUMENTS

CN    105987867 A   10/2016
CN    107037178 A    8/2017
(Continued)

OTHER PUBLICATIONS

Cheng et al., "Design and fabrication of piezoelectric actuated valve micropump and its application in electronic cooling", <http://aoiea.itri.org.tw/files/columnist/20130503180526024310/file/1/B09-2.pdf>, 14 total pages.
(Continued)

*Primary Examiner* — Charles G Freay
*Assistant Examiner* — Lilya Pekarskaya
(74) *Attorney, Agent, or Firm* — Birch, Stewart, Kolasch & Birch, LLP

(57) ABSTRACT

An actuating and sensing module is disclosed and includes an actuating device, a first substrate, a second substrate, a valve membrane and a sensor stacked sequentially. The first substrate includes an intake channel, an exhaust channel, an inlet and an outlet. The valve membrane is disposed between the first substrate and the second substrate and includes an intake valve and an exhaust valve to insulate the intake channel and the exhaust channel, respectively. The actuating device is disposed to seal a through slot of the second substrate to form a compressing chamber. The inlet, the intake channel, the compressing chamber, the exhaust channel and the outlet are in communication with each other to define a gas flow loop. The sensor is disposed in the gas flow loop. While the actuating device drives gas from the outside, the gas is transported into the gas flow loop and sensed by the sensor.

19 Claims, 6 Drawing Sheets

(51) Int. Cl.
  *G01N 1/22* (2006.01)
  *B81B 3/00* (2006.01)
  *H01L 41/09* (2006.01)

(52) U.S. Cl.
  CPC .... *G01N 33/0009* (2013.01); *B81B 2201/036* (2013.01); *B81B 2203/0127* (2013.01); *B81B 2203/053* (2013.01); *F05B 2220/709* (2013.01); *H01L 41/0926* (2013.01)

(58) Field of Classification Search
  CPC ....... B81B 2203/0127; B81B 2203/053; F05B 2220/709; H01L 41/0926
  See application file for complete search history.

(56) References Cited

U.S. PATENT DOCUMENTS

| | | | | |
|---|---|---|---|---|
| 7,495,300 | B2* | 2/2009 | Gardner | G01N 27/128 257/252 |
| 2005/0199041 | A1* | 9/2005 | Weber | G01N 27/128 73/31.06 |
| 2009/0242060 | A1* | 10/2009 | Chen | F04B 45/04 137/814 |
| 2013/0058819 | A1* | 3/2013 | Kodama | F04B 45/047 417/479 |
| 2014/0377099 | A1* | 12/2014 | Hsueh | F04B 49/22 417/413.2 |

FOREIGN PATENT DOCUMENTS

| | | | |
|---|---|---|---|
| CN | 107023461 A | 9/2017 | |
| EP | 2733484 A1 | 5/2014 | |
| EP | 2998582 A1 | 3/2016 | |
| TW | M525446 U | 7/2016 | |
| TW | M538545 U | 3/2017 | |
| TW | M543870 U | 6/2017 | |
| TW | M544653 U | 7/2017 | |
| WO | WO 2012/154029 A1 | 11/2012 | |
| WO | WO-2012154029 A1 * | 11/2012 | ......... G01N 33/0009 |
| WO | WO 2017/072489 A1 | 5/2017 | |

OTHER PUBLICATIONS

Extended European Search Report, dated Feb. 12, 2019, for European Application No. 18184963.9.

* cited by examiner

ACTUATING AND SENSING MODULE

FIELD OF THE INVENTION

The present disclosure relates to an actuating and sensing module, and more particularly to an actuating and sensing module sensing gas by means of gas circulation.

BACKGROUND OF THE INVENTION

Nowadays, people pay much attention to monitoring environmental air quality in daily living, e.g., monitoring carbon monoxide, carbon dioxide, volatile organic compounds (VOC), PM2.5, and so on. The exposure of these substances in the environment can cause human health problems or can even harm the life. Therefore, it has become an important issue for every country to develop and implement environmental air quality monitoring technology.

However, the conventional gas detection equipment for example an air cleaning and filtering apparatus is bulky in volume and is not suitable to be carried by the user. Consequently, it is difficult for the user to obtain the real-time air quality information relating to the surrounding environment, and the user is still likely to be exposed to an environment with harmful gases. Therefore, an urgent problem that needs to be solved is how to obtain the gas quality information relating to the surrounding environment at anytime and anywhere.

However, since the conventional gas detection equipment fails to provide the waterproof and dustproof functions, some problems occur. If moisture or liquid is introduced into the equipment during the process of transferring the gas, the outputted gas tends to contain the moisture, so that the electronic components utilized to sense the gas is possibly damped, rusted or damaged. Moreover, the conventional gas detection equipment fails to provide dustproof function. If dust is introduced into the gas detection equipment during the process of transferring the gas, the components are possibly damaged and the gas transportation efficiency is reduced. Therefore, another urgent problem that needs to be solved is how to make the gas detection equipment has the waterproof and dustproof benefits.

Therefore, there is a need of providing an actuating and sensing module for allowing a gas detection apparatus or equipment to achieve small-size, miniature, silent, waterproof and dustproof benefits in order to eliminate the above drawbacks.

SUMMARY OF THE INVENTION

An object of the present disclosure provides an actuating and sensing module. While the gas fluctuation is generated by the high frequency operation of the piezoelectric membrane, a pressure gradient is generated in the designed flow channel and the gas flows at a high speed. Moreover, since there is an impedance difference between the feeding direction and the exiting direction, the gas can be transported from the inlet side to the outlet side. It benefits to solve the problems that the apparatus or equipment utilizing the conventional gas transportation device has a large volume, is difficult to be thinned, fails to achieve the purpose of portability, and has loud noises.

Another object of the present disclosure provides an actuating and sensing module with waterproof and dustproof functions. By being equipped with a protective film to filter the moisture and the dust, it benefits to solve the problems that while the moisture or the dust is introduced into the conventional gas transportation device during the process of transferring the gas, the components are possibly damaged and the gas transportation efficiency is reduced.

In accordance with an aspect of the present disclosure, an actuating and sensing module is provided. The actuating and sensing module includes a first substrate, a second substrate, a valve membrane, an actuating device and a sensor. The first substrate includes an intake channel, an exhaust channel, an inlet and an outlet, wherein the intake channel and the exhaust channel are in communication with an outside of the first substrate through the inlet and the outlet, respectively. The second substrate includes a through slot, wherein the through slot is open setting. The valve membrane includes an intake valve and an exhaust valve, wherein the valve membrane is disposed between the first substrate and the second substrate, and the intake valve and the exhaust valve are configured to close and insulate the intake channel and the exhaust channel, respectively. The actuating device is disposed in the second substrate and covers the through slot, so as to form a compressing chamber between the valve membrane and the through slot of the second substrate, wherein the inlet, the intake channel, the compressing chamber, the exhaust channel and the outlet are in communication with each other to form a gas flow loop. The sensor is disposed in the gas flow loop. While the actuating device drives the intake valve of the valve membrane to vibrate upwardly and be opened, a gas is inhaled from outside into the intake channel through the inlet and transferred to the compressing chamber through the intake valve. While the actuating device compresses the compressing chamber and drives the exhaust valve of the valve membrane to vibrate downwardly and to be opened, the gas is transferred to the exhaust channel and discharged out through the outlet, so that the gas circulated in the gas flow loop is sensed by the sensor.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1A:
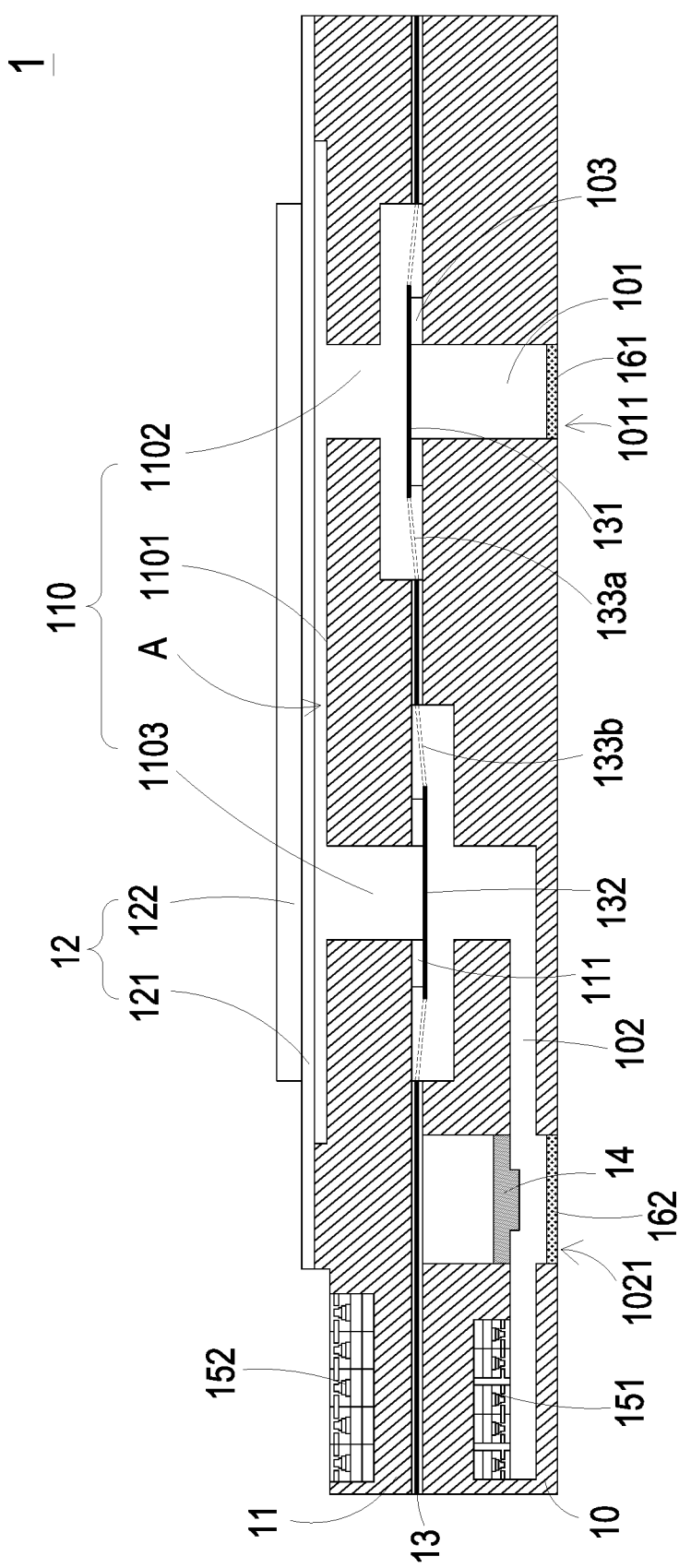
FIG. 1A is a cross-sectional view illustrating an actuating and sensing module according to a first embodiment of the present disclosure.
Figure 1B:
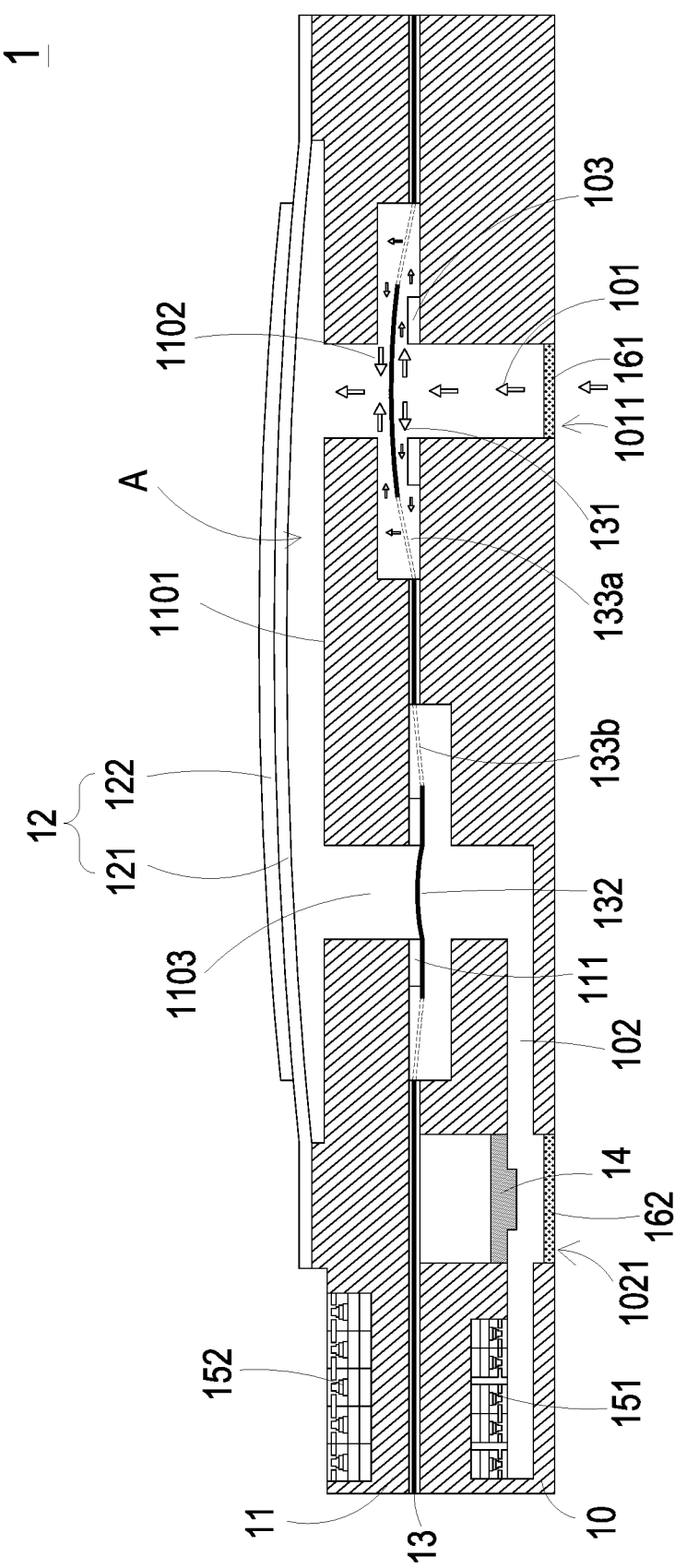
FIG. 1B is a cross-sectional view illustrating a gas-intake operation of the actuating and sensing module according to the first embodiment of the present disclosure.
Figure 1C:
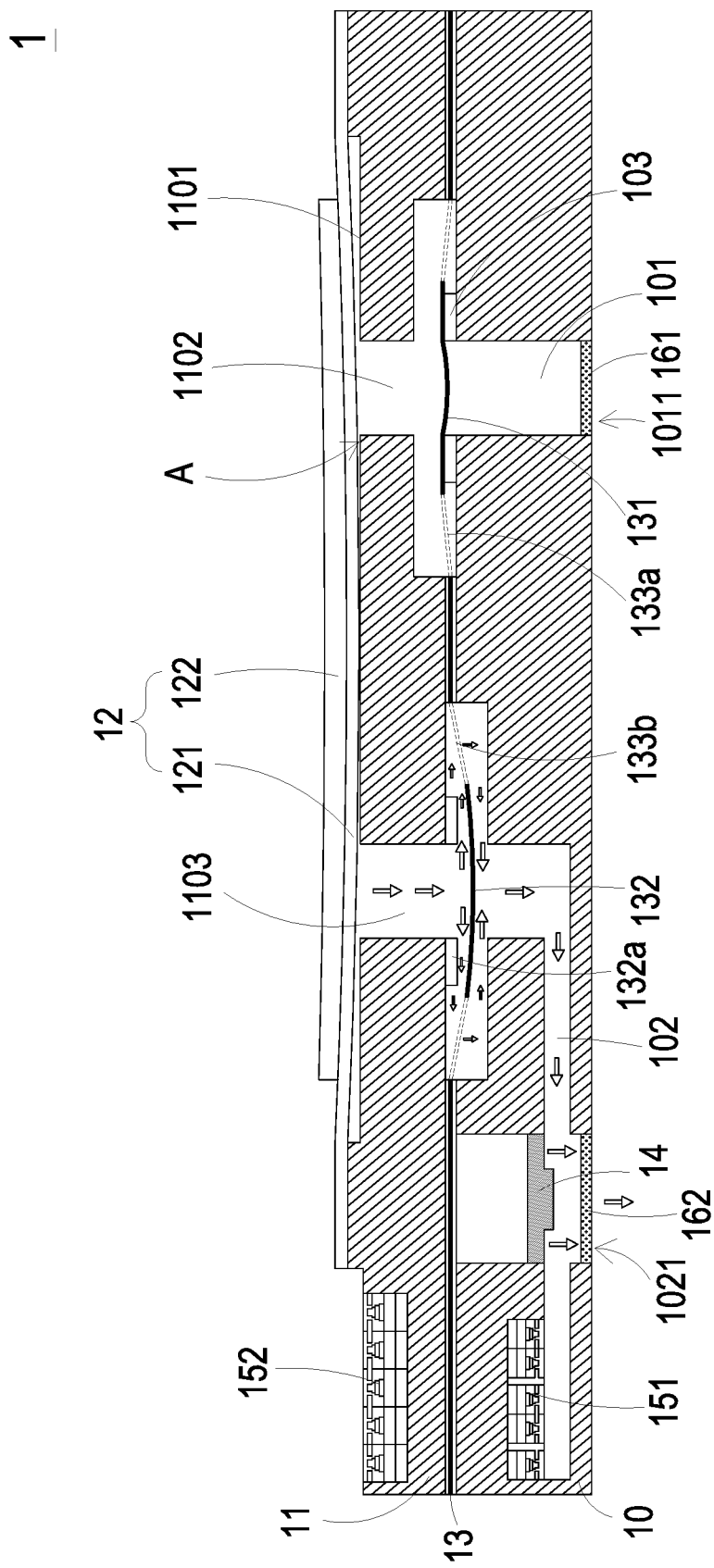
FIG. 1C is a cross-sectional view illustrating a gas-exhaust operation of the actuating and sensing module according to the first embodiment of the present disclosure.

Please refer to FIGS. 1A to 1C. The present discourse provides an actuating and sensing module 1 including at least one first substrate 10, at least one intake channel 101, at least one exhaust channel 102, an inlet 1011, an outlet 1021, at least one second substrate 11, at least one through slot 10, at least one valve membrane 13, at least one intake valve 131, at least one exhaust valve 132, at least one actuating device 12, at least one compressing chamber A, at least one gas flow loop, at least one sensor 14 and at least one gas. The number of the first substrate 10, the intake channel 101, the exhaust channel 102, the inlet 1011, the outlet 1021, the second substrate 11, the through slot 110, the valve membrane 13, the intake valve 131, the exhaust valve 132, the actuating device 12, the compressing chamber A, the gas flow loop, the sensor 14 and the gas is exemplified by one for each in the following embodiments but not limited thereto. It is noted that each of the first substrate 10, the intake channel 101, the exhaust channel 102, the inlet 1011, the outlet 1021, the second substrate 11, the through slot 110, the valve membrane 13, the intake valve 131, the exhaust valve 132, the actuating device 12, the compressing chamber A, the gas flow loop, the sensor 14 and the gas can also be provided in plural numbers.

The present disclosure provides an actuating and sensing module, which is used to sense the air quality relating to the surrounding environment and has the waterproof, dustproof and silent benefits. The actuating and sensing module may be used in a mobile phone, a tablet, a wearable device or any similar portable electronic device constructed to contain CPU, RAM and other components. Please refer to FIG. 1, which is a cross-sectional view illustrating an actuating and sensing module according to a first embodiment of the present disclosure. As shown in the drawing, the actuating and sensing module 1 includes a first substrate 10, a second substrate 11, an actuating device 12, a valve membrane 13 and a sensor 14. The first substrate 10 includes an intake channel 101 and an exhaust channel 102 running therethrough. The intake channel 101 and the exhaust channel 102 includes an inlet 1011 and an outlet 1021 disposed on an outer surface of the first substrate 10, respectively. The second substrate 11 includes a through slot 110 running therethrough, wherein the through slot 110 is open setting. In the embodiment, the through slot 110 includes a recess 1101, a second intake channel 1102 and a second exhaust channel 1103, and the second intake channel 1102 and the second exhaust channel 1103 run through the recess 1101, respectively. While the first substrate 10 and the second substrate 11 are stacked and assembled together, the second intake channel 1102 and the second exhaust channel 1103 of the second substrate 11 are aligned with the intake channel 101 and the exhaust channel 102 of the first substrate 10, respectively.

In this embodiment, the first substrate 10 and the second substrate 11 can be for example but not limited to an application-specific integrated circuit (ASIC) chip or a system-on-chip (SOC) chip. The intake channel 101 and the exhaust channel 102 of the first substrate 10 are formed by a semiconductor process. Moreover, the through slot 110 of the second substrate 11 is formed by a semiconductor process. The first substrate 10 and the second substrate 11 are combined together by a package process.

In this embodiment, a first control circuit 151 is formed on the first substrate 10 by a semiconductor process, and a second control circuit 152 is formed on the second substrate 11 by a semiconductor process. The first control circuit 151 and the second control circuit 152 are an integrated circuit, respectively. Meanwhile, the first control circuit 151 is electrically connected to the sensor 14, so as to calculate and process the sensed data generated by the sensor 14. The second control circuit 152 is electrically connected to the actuating device 12, so as to provide a driving power to the actuating device 12. In other embodiments, one of the first substrate 10 and the second circuit 11 includes a control circuit merely, and the single control circuit is electrically connected to the actuating device 12 and the sensor 14, so as to provide a driving power to the actuating device 12, calculate and process the sensed data generated by the sensor 14.

Please refer to FIG. 1A. The actuating device 12 is used to drive gas and disposed to seal the through slot 110 of the second substrate 11, so as to define a compressing chamber A between the through slot 110 and the valve membrane 13. In this embodiment, the actuating device 12 can be a microelectromechanical system (MEMS) gas pump, and the surface of the material is micro-machined by means of dry and wet etching, so as to make an integrally formed miniature gas pump. The actuating device 12 includes an actuating membrane 121 and a piezoelectric membrane 122. The actuating membrane 121 includes a flat structure made by a surface micromachining process. The material of the actuating membrane 121 can be a metallic membrane or a polysilicon membrane. The material of the actuating membrane 121 is not limited to the above embodiments and can be varied according to the practical requirements. The piezoelectric membrane 122 can be a metal oxide membrane made by a sol-gel process and attached on a surface of the actuating membrane 121. When the piezoelectric member 122 is enabled to drive the actuating membrane 121 to vibrate upwardly, a pressure gradient is generated in the compressing chamber A for allowing the gas to flow from the intake channel 101 into the compressing chamber A through the second intake channel 1102 (as shown in FIG. 1B). On the contrary, when the piezoelectric membrane 122 is enabled to drive the actuating membrane 121 to vibrate downwardly, the compressing chamber A is compressed for allowing the gas to flow from the compressing chamber A into the exhaust channel 102 through the second exhaust channel 1103 (as shown in FIG. 1C). With the piezoelectric membrane 122 vibrating along a vertical direction in a reciprocating manner, the gas can be driven to flow at high speed. Moreover, since there is an impedance difference between the feeding direction and the exiting direction, the gas can be transported from the inlet side to the outlet side. Even if a gas pressure exists at the outlet side, the actuating device 12 still has the capability of pushing the gas to the outlet side while achieving the silent efficacy.

Please refer to FIG. 1A again. The valve membrane 13 is disposed between the first substrate 10 and the second substrate 11 and includes an intake valve 131 and an exhaust valve 132, which both include an openable and closeable valve switch structure. In a valve-closed state, the intake channel 101 of the first substrate 10 is closed by the intake valve 131 so as to insulate the intake channel 101 and the second intake channel 1102, and the exhaust channel 102 of the first substrate 10 is closed by the exhaust valve 132 so as to insulate the exhaust channel 102 and the second exhaust channel 1103. In a valve-opened state, the second intake channel 1102 is in communication with the intake channel 101 of the first substrate 10, and the second exhaust channel 1103 is in communication with the exhaust channel 102 of the first substrate 10, so that the inlet 1011, the intake channel 101, the compressing chamber A, the exhaust channel 102 and the outlet 1021 are in communication with each other to form a gas flow loop.

As shown in FIG. 1A, in the embodiment, the valve membrane 13 includes a flexible membrane structure and includes a plurality of perforations 133a, 133b, which are used for forming the intake valve 131 and the exhaust valve 132. In response to the gas pressure, the flexible membrane structures of the intake valve 131 and the exhaust valve 132 are subjected to the curvy deformation to open, so that the perforations 133a, 133b located at the peripheral regions of the flexible membrane structures allow the gas to flow therethrough. Furthermore, the first substrate 10 includes a convex structure 103 aligned with the intake valve 131, so as to generate a pre-force to abut against the intake valve 131. Similarly, the second substrate 11 includes a convex structure 111 aligned with the exhaust valve 132, so as to generate a pre-force to abut against the exhaust valve 132. Due to the arrangement of the convex structure 103 and the convex structure 111, it prevents the gas in the gas flow loop from being reversely returned through the intake valve 131 and the exhaust valve 132.

Please refer to FIG. 1A. The sensor 14 is disposed at any position in the gas flow loop described above so as to sense the gas. In this embodiment, the sensor 14 is disposed on one of the first substrate 10 and the second substrate 11 by a semiconductor process and in contact with or adjacent to the gas flow loop. In the embodiment, the sensor 14 is disposed in the exhaust channel 102 of the first substrate 10 and aligned with the outlet 1021. In the embodiment, the sensor 14 is electrically connected to the first control circuit 151 so as to obtain a driving power and sense a concentration of at least one target contained in the gas in the gas flow loop. The sensor 14 can include at least one selected from the group consisting of an oxygen sensor, a carbon monoxide sensor, a carbon dioxide sensor, a temperature sensor, an ozone sensor, a volatile organic compound sensor and a combination thereof, but not limited thereto. It can be varied according to the practical requirements.

Please refer to FIGS. 1A, 1B and 1C. FIG. 1B is a cross-sectional view illustrating a gas-intake operation of the actuating and sensing module according to the first embodiment of the present disclosure. FIG. 1C is a cross-sectional view illustrating a gas-exhaust operation of the actuating and sensing module according to the first embodiment of the present disclosure. As shown in FIG. 1A, the actuating and sensing module 1 is in a disable state. When the actuating and sensing module 1 is enabled, a driving power is provided to the actuating device 12 by the second control circuit 152, so that the actuating device 12 is enabled to vibrate along a vertical direction in a reciprocating manner. As shown in FIG. 1B, when the actuating device 12 vibrates upwardly, the volume of the compressing chamber A is increased and the pressure of the compressing chamber A is decreased. Under this circumstance, a pressure gradient occurs to drive the intake valve 131 of the valve membrane 13 to vibrate upwardly and be opened. Meanwhile, the exhaust valve 132 of the valve membrane 13 maintains to close and abuts against the convex structure 111. In this way, an external gas is fed into the intake channel 101 through the inlet 1011, and the gas is transferred to the compressing chamber A through the plurality of perforations 133a of the valve membrane 13. On the contrary, as shown in FIG. 1C, when the actuating device 12 vibrates downwardly, the volume of the compressing chamber A is decreased and the pressure of the compressing chamber A is increased. Under this circumstance, a pressure gradient occurs to drive the exhaust valve 132 of the valve membrane 13 to vibrate downwardly and open. At the same time, the intake valve 131 of the valve membrane 13 vibrates downwardly to abut against the convex structure 103 and be closed. In this way, the gas in the compressing chamber A is transferred into the exhaust channel 102 through the plurality of perforations 133b of the valve membrane 13, and discharged out of the actuating and sensing module 1 through the outlet 1021.

With the arrangement of the intake valve 131 and the exhaust valve 132 of the valve membrane 13, two valves are operated in reverse and the gas is transferred along one direction in the gas flow loop. It will not generate the phenomenon of reverse flow. In this way, since the gas in the gas flow loop is transferred to the sensor 14 continuously, the sensor 14 can be used for monitoring a concentration of at least one target contained in the ambient air, so as to obtain the real-time information relating to the ambient air at anytime and anywhere. Moreover, while the speed of the gas circulation is accelerated by the actuating device 12, and the sensor 14 can obtain the most immediate information relating to the ambient air. That is, once it is detected that the surrounding environment contains toxic gases or dangerous gases, the user can be notified to take immediate protective measures to avoid the gas poisoning and the gas explosion.

Please refer to FIG. 1A again. In this embodiment, the actuating and sensing module 1 further includes a first protective membrane 161 and a second protective membrane 162. The first protective membrane 161 is disposed to cover the inlet 1011 of the first substrate 10 and the second protective membrane 162 is disposed to cover the outlet 1021 of the first substrate 10. Since the first protective membrane 161 and the second protective membrane 162 are a waterproof, dustproof and gas-allowed film structure, the arrangement prevents the moisture and dust from entering the gas flow loop through the inlet 1011 or the outlet 1021. Thus, the inner space of the actuating and sensing module 1 can be maintained in a dry and dust-free situation. It benefits to prevent the components disposed inside the gas flow loop from the damage and the rusty caused by the moisture or the accumulated dust. In addition, the first protective membrane 161 and the second protective membrane 162 comply with the Rating IP64 of International Protection Marking (IEC 60529), i.e., Dust protection level 6 (Complete protection, No ingress of dust) and Water protection level 4 (Protection against Splashing of water: Water splashing against the enclosure from any direction shall have no harmful effect). In another embodiment, the first protective membrane 161 and the second protective membrane 162 comply with the Rating IP68 of International Protection Marking (IEC 60529), i.e., Dust protection level 6 and Water protection level 8 (Continuous immersion in water produces no harmful effects). In other embodiments, the first protective membrane 161 and the second protective membrane 162 comply with the Rating IP65, IP66 or IP67 of International Protection Marking (IEC 60529), but not limited thereto.

Figure 2A:
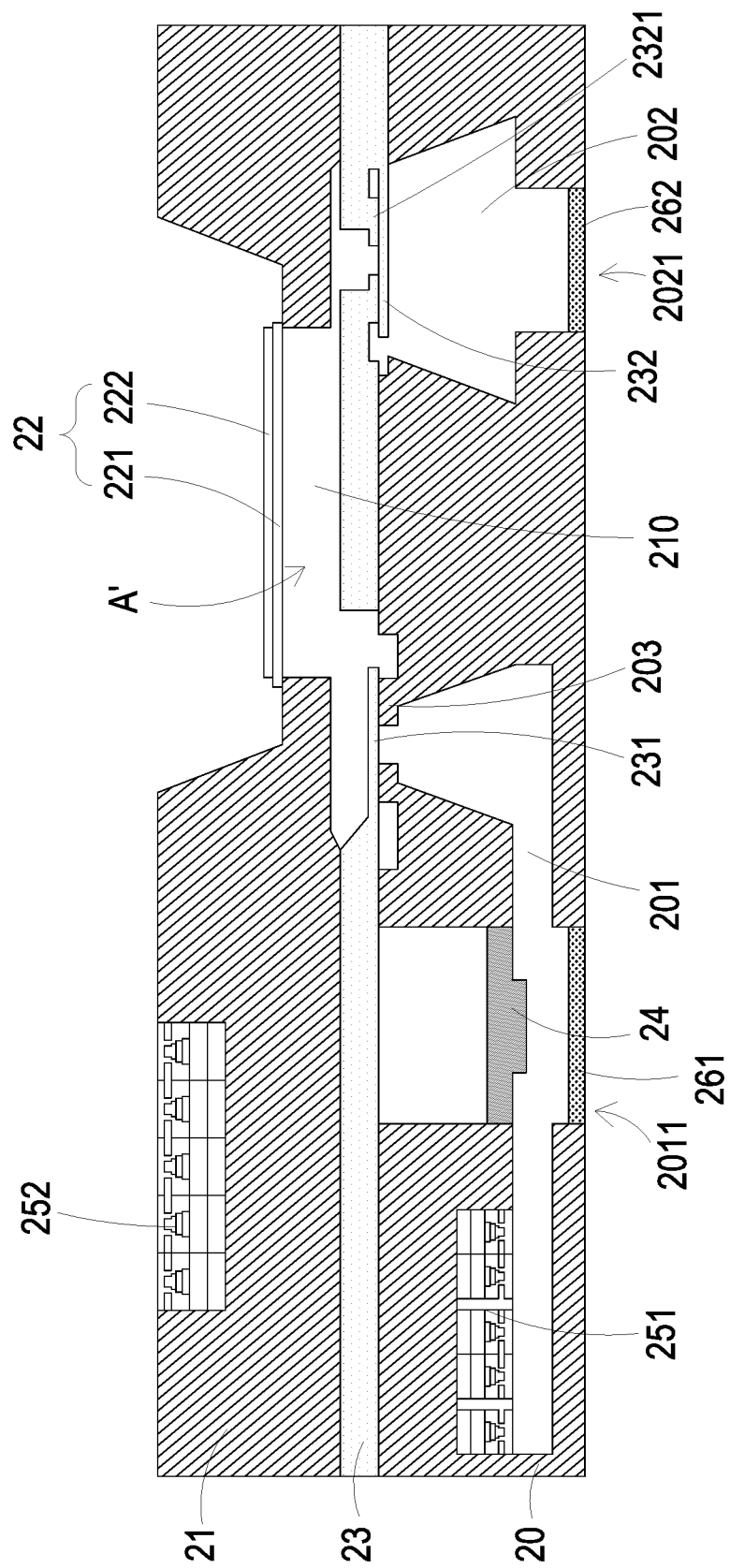
FIG. 2A is a cross-sectional view illustrating an actuating and sensing module according to a second embodiment of the present disclosure.

Please refer to FIG. 2A. FIG. 2A is a cross-sectional view illustrating an actuating and sensing module according to a second embodiment of the present disclosure. As shown in the drawing, in the embodiment, the actuating and sensing module 2 includes a first substrate 20, a second substrate 21, an actuating device 22, a valve membrane 23 and a sensor 24. The first substrate 20 includes an intake channel 201 and an exhaust channel 202 running therethrough. The intake channel 201 and the exhaust channel 202 includes an inlet

2011 and an outlet 2021 disposed on an outer surface of the first substrate 21, respectively. The second substrate 21 includes a through slot 210 running therethrough, wherein the through slot 210 is open setting. While the first substrate 20 and the second substrate 21 are stacked and assembled together, the intake channel 201 and the exhaust channel 202 of the first substrate 20 are in communication with the through slot 210 of the second substrate 21.

Please refer to FIG. 2A. In the embodiment, a first control circuit 251 is formed on the first substrate 20 by a semiconductor process, and a second control circuit 252 is formed on the second substrate 21 by a semiconductor process. The first control circuit 251 is electrically connected to the sensor 24, so as to calculate and process the sensed data generated by the sensor 24. The second control circuit 252 is electrically connected to the actuating device 22, so as to provide a driving power to the actuating device 22. The actuating device 22 is disposed on the second substrate 21 and seals the through slot 210, so as to define a compressing chamber A' between the through slot 210 and the valve membrane 23.

Please refer to FIG. 2A again. The valve membrane 23 is disposed between the first substrate 20 and the second substrate 21 and includes an intake valve 231 and an exhaust valve 232, which both include an openable and closeable valve switch structure. In a valve-closed state, the intake channel 201 of the first substrate 20 is closed by the intake valve 231 so as to insulate the intake channel 201 and the through slot 210, and the exhaust channel 202 of the first substrate 20 is closed by the exhaust valve 232 so as to insulate the exhaust channel 202 and the through slot 210. In a valve-opened state, the through slot 210 is in communication with the intake channel 201 of the first substrate 20, and the through slot 210 is in communication with the exhaust channel 202 of the first substrate 20, so that the inlet 2011, the intake channel 201, the compressing chamber A', the exhaust channel 202 and the outlet 2021 are in communication with each other to form a gas flow loop.

In the embodiment, the first substrate 20 further includes a circular groove aligned with the intake valve 231, wherein the circular groove is open setting, so as to form a convex structure 203, which provides a pre-force to abut against the intake valve 231. Similarly, the valve membrane 23 further includes a circular groove aligned with the exhaust valve 232, wherein the circular groove is open setting, so as to form a convex structure 2321, which provides a pre-force to abut against the exhaust valve 232. Due to the arrangement of the convex structure 203 and the convex structure 2321, it prevents the gas in the gas flow loop from being reversely returned through the intake valve 231 and the exhaust valve 232.

In the embodiment, the actuating device 22 can be a piezoelectric actuator including the similar structure and actions in the foregoing embodiment. In the embodiment, the sensor 24 is disposed in the intake channel 201 of the second substrate 21 and aligned with the inlet 2011. The sensor 24 is further electrically connected to the first control circuit 251 so as to obtain the driving power.

Figure 2B:
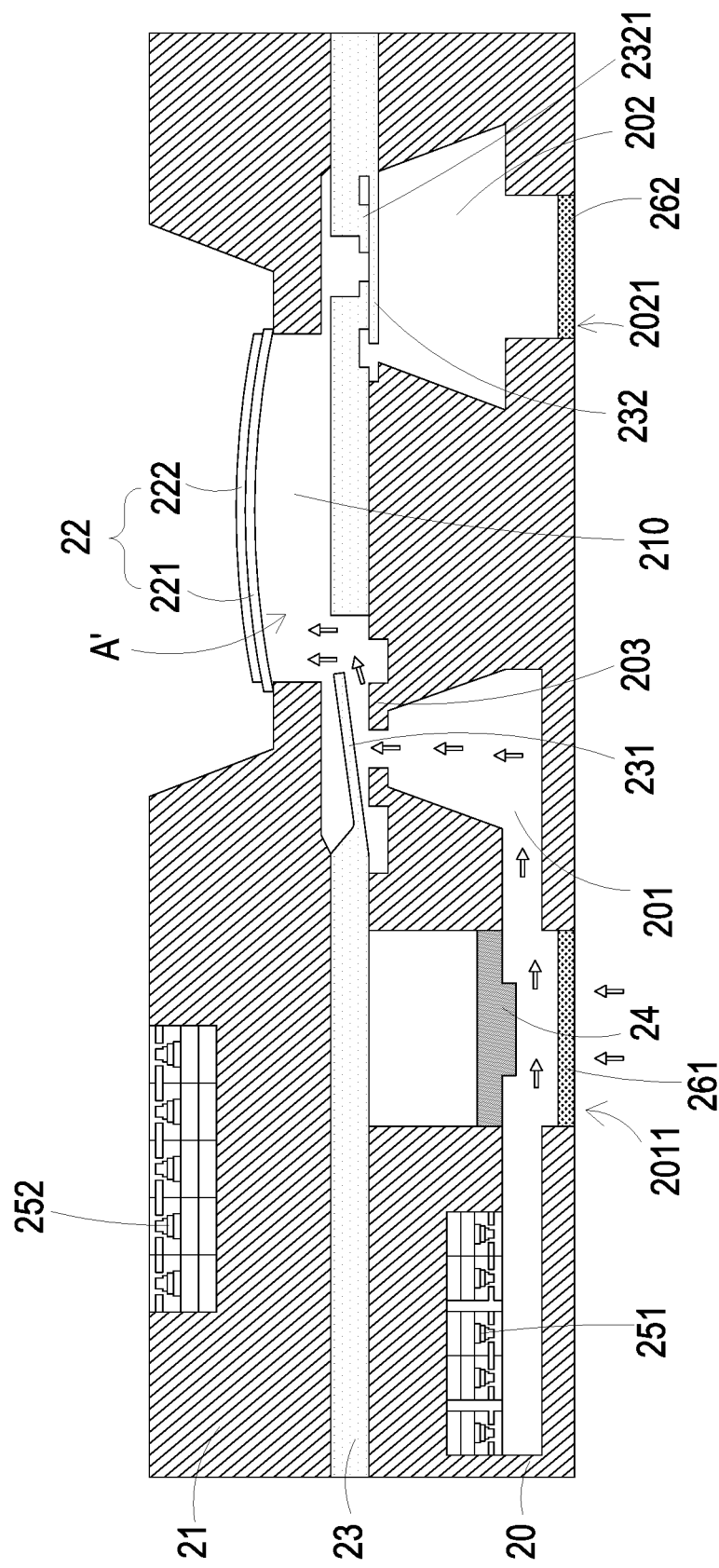
FIG. 2B is a cross-sectional view illustrating a gas-intake operation of the actuating and sensing module according to the second embodiment of the present disclosure.
Figure 2C:
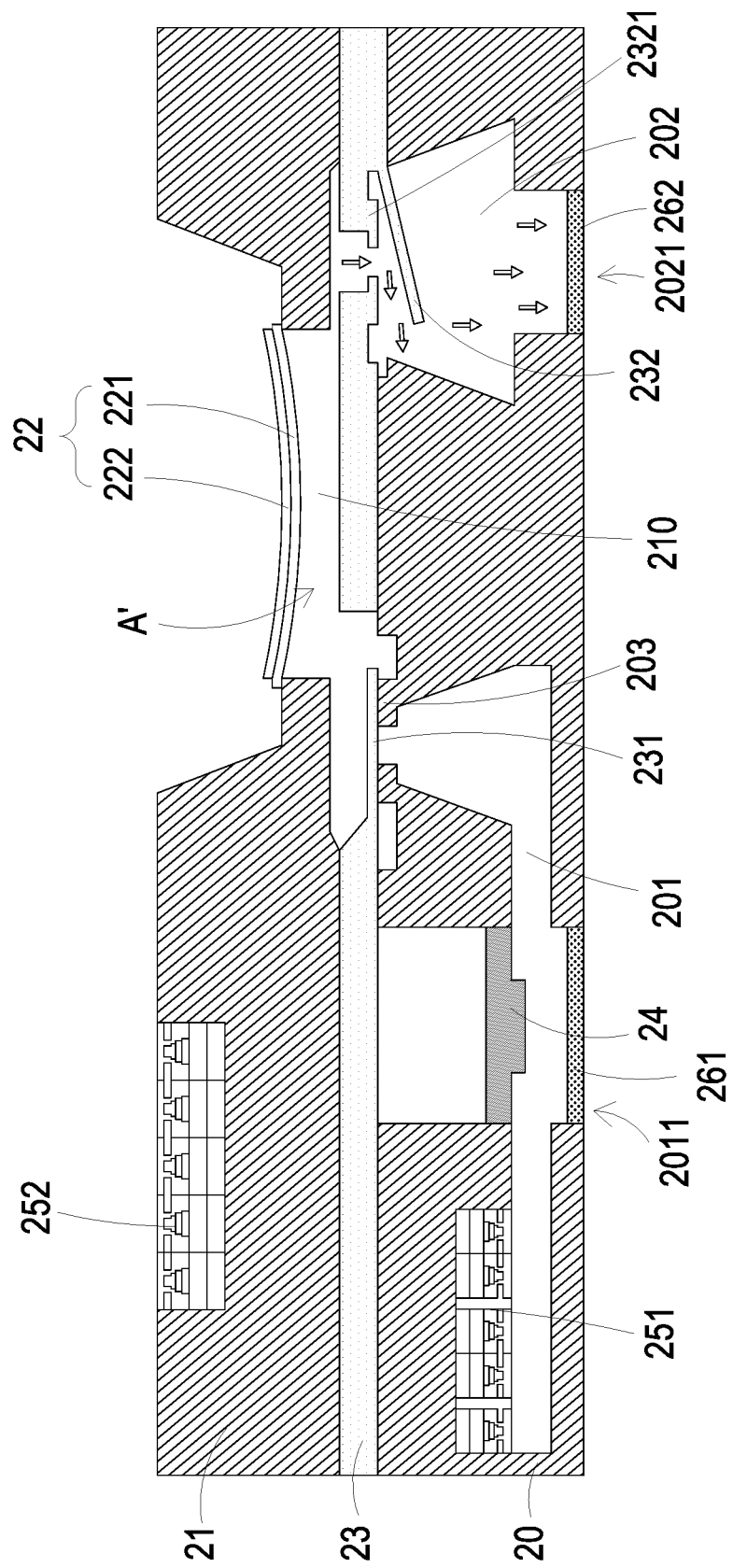
FIG. 2C is a cross-sectional view illustrating a gas-exhaust operation of the actuating and sensing module according to the second embodiment of the present disclosure.

Please refer to FIGS. 2A, 2B and 2C. FIG. 2B is a cross-sectional view illustrating a gas-intake operation of the actuating and sensing module according to the second embodiment of the present disclosure. FIG. 2C is a cross-sectional view illustrating a gas-exhaust operation of the actuating and sensing module according to the second embodiment of the present disclosure. As shown in FIG. 2A, the actuating and sensing module 2 is in a disable state. When the actuating and sensing module 2 is enabled, a driving power is provided to the actuating device 22 by the second control circuit 252, so that the actuating device 22 is enabled to vibrate along a vertical direction in a reciprocating manner. As shown in FIG. 2B, when the actuating device 22 vibrates upwardly, the volume of the compressing chamber A' is increased and the pressure of the compressing chamber A' is decreased. Under this circumstance, a pressure gradient occurs to drive the intake valve 231 of the valve membrane 23 to vibrate upwardly and be opened. Meanwhile, the exhaust valve 232 of the valve membrane 23 maintains to close and abuts against the convex structure 2321. In this way, an external gas is fed into the intake channel 201 through the inlet 2011, and the gas is transferred to the compressing chamber A' through the intake valve 231. On the contrary, as shown in FIG. 2C, when the actuating device 22 vibrates downwardly, the volume of the compressing chamber A' is decreased and the pressure of the compressing chamber A' is increased. Under this circumstance, a pressure gradient occurs to drive the exhaust valve 232 of the valve membrane 23 to vibrate downwardly and open. At the same time, the intake valve 231 of the valve membrane 23 vibrates downwardly to abut against the convex structure 203 and be closed. In this way, the gas in the compressing chamber A' is transferred into the exhaust channel 202 through the exhaust valve 232 of the valve membrane 23, and discharged out of the actuating and sensing module 2 through the outlet 2021.

Please refer to FIGS. 2A to 2C again. In the embodiment, the actuating and sensing module 2 further includes a first protective first protective membrane 261 and a second protective membrane 262. The first protective membrane 261 is disposed to cover the inlet 2011 of the first substrate 20 and the second protective membrane 262 is disposed to cover the outlet 2021 of the first substrate 20. Since the first protective membrane 261 and the second protective membrane 262 are a waterproof dustproof and gas-allowed film structure, the arrangement prevents the moisture and dust from entering the gas flow loop through the inlet 2011 or the outlet 2021. Thus, the inner space of the actuating and sensing module 2 can be maintained in a dry and dust-free situation. It benefits to prevent the components disposed inside the gas flow loop from the damage and the rusty caused by the moisture or the accumulated dust. In addition, the first protective membrane 261 and the second protective membrane 262 comply with the Rating IP64 of International Protection Marking (IEC 60529). i.e., Dust protection level 6 (Complete protection, No ingress of dust) and Water protection level 4 (Protection against Splashing of water: Water splashing against the enclosure from any direction shall have no harmful effect). In another embodiment, the first protective membrane 261 and the second protective membrane 262 comply with the Rating IP68 of international Protection Marking (IEC 60529), i.e., Dust protection level 6 and Water protection level 8 (Continuous immersion in water produces no harmful effects). In other embodiments, the first protective membrane 261 and the second protective membrane 262 comply with the Rating IP65, IP66 or IP67 of International Protection Marking (IEC 60529), but not limited thereto.

From the above descriptions, the present disclosure provides the actuating and sensing module. With the actuating membrane activated by the piezoelectric membrane, a pressure gradient is generated in the compressing chamber for allowing the gas to be transported at a high speed. Under this circumstance, the gas flow loop is achieved, and the gas can be quickly transferred while achieving silent efficacy. With the sensor for sensing the gas, the most immediate information relating to the ambient air can be obtained at anytime and anywhere. In addition, due to the arrangement of the first protective film and the second protective film, it prevents the inner components from the damage and the rusty caused by the moisture or the accumulated dust. Consequently, the gas transportation efficiency is enhanced and the performance of the device with the actuating and sensing module is enhanced. Therefore, the actuating and sensing module of the present disclosure is industrially valuable.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An actuating and sensing module comprising:
   a first substrate comprising an intake channel, an exhaust channel, an inlet and an outlet, wherein the intake channel and the exhaust channel are in communication with an outside of the first substrate through the inlet and the outlet, respectively;
   a second substrate comprising a through slot, wherein the through slot is disposed in its open setting;
   a valve membrane comprising an intake valve and an exhaust valve, wherein the valve membrane is disposed between the first substrate and the second substrate, and the intake valve and the exhaust valve are configured to close and insulate the intake channel and the exhaust channel, respectively;
   an actuating device disposed in the second substrate and covering the through slot, so as to form a compressing chamber between the valve membrane and the through slot of the second substrate, wherein the inlet, the intake channel, the compressing chamber, the exhaust channel and the outlet are in communication with each other to form a gas flow loop; and
   a sensor disposed in the gas flow loop;
   wherein, while the actuating device is enabled to drive the intake valve of the valve membrane to vibrate upwardly and be opened, a gas is inhaled from outside into the intake channel through the inlet of the first substrate and transferred to the compressing chamber through the intake valve of the valve membrane,
   wherein, while the actuating device compresses the gas in the compressing chamber and drives the exhaust valve of the valve membrane to vibrate downwardly and to be opened, the gas is transferred to the exhaust channel and discharged out through the outlet of the first substrate, so that the gas circulated in the gas flow loop is sensed by the sensor,
   wherein the first substrate further comprises a first protective membrane and a second protective membrane, wherein the first protective membrane is disposed to cover the inlet of the first substrate, and the second protective membrane is disposed to cover the outlet of the first substrate, wherein the first protective membrane and the second protective membrane includes a waterproof, dustproof and gas-allowed film structure, respectively.

2. The actuating and sensing module according to claim 1, wherein the sensor is disposed in the intake channel and aligned with the inlet of the first substrate.

3. The actuating and sensing module according to claim 1, wherein the sensor is disposed in the exhaust channel and aligned with the outlet of the first substrate.

4. The actuating and sensing module according to claim 1, wherein the sensor is disposed on one of the first substrate and the second substrate by a semiconductor process.

5. The actuating and sensing module according to claim 1, wherein the intake channel and the exhaust channel of the first substrate are formed by a semiconductor process and the through slot of the second substrate is formed by a semiconductor process.

6. The actuating and sensing module according to claim 1, wherein the first substrate comprises a first control circuit formed by a semiconductor process, and the second substrate comprises a second control circuit formed by a semiconductor process, wherein the sensor is electrically connected to the first control circuit so as to transmit a sensed data generated by the sensor to the first control circuit to be calculated and processed, and the actuating device is electrically connected to the second control circuit so as to obtain a driving power.

7. The actuating and sensing module according to claim 1, wherein the intake valve and the exhaust valve include an openable and closeable valve switch structure, respectively.

8. The actuating and sensing module according to claim 1, wherein the valve membrane is a flexible membrane.

9. The actuating and sensing module according to claim 8, wherein the valve membrane further comprises a plurality of perforations, wherein the plurality of the perforations are disposed around peripheral regions of the intake valve and the exhaust valve for allowing the gas to flow therethrough.

10. The actuating and sensing module according to claim 9, wherein the first substrate further comprises a convex structure aligned with the intake valve to provide a pre-force to abut against the intake valve and the second substrate further comprises a convex structure aligned with the exhaust valve to provide a pre-force to abut against the exhaust valve, so as to prevent the gas from being reversely returned.

11. The actuating and sensing module according to claim 8, wherein one of the intake valve and the exhaust valve further comprises a convex structure to provide a pre-force to abut against one of the intake valve and the exhaust valve, so as to prevent the gas from being reversely returned.

12. The actuating and sensing module according to claim 1, wherein the sensor includes at least one selected from the group consisting of an oxygen sensor, a carbon monoxide sensor, a carbon dioxide sensor, a temperature sensor, an ozone sensor, a volatile organic compound sensor and a combination thereof.

13. The actuating and sensing module according to claim 1, wherein the actuating device is a microelectromechanical system gas pump integrally formed and comprises:
   an actuating membrane including a flat structure made by a surface micromachining process and formed by one of a metallic membrane and a polysilicon membrane; and
   a piezoelectric membrane including a metal oxide membrane made by a sol-gel process and attached on a surface of the actuating membrane;
   wherein, while the piezoelectric membrane is enabled to drive the actuating membrane to vibrate upwardly, a pressure gradient is generated in the compressing chamber for allowing the gas to flow from the intake channel into the compressing chamber, wherein while the piezoelectric membrane is enabled to drive the actuating membrane to vibrate downwardly, the gas in the compressing chamber is compressed and further flows from the compressing chamber to the exhaust channel.

14. The actuating and sensing module according to claim 1, wherein the first protective membrane and the second protective membrane comply with Rating IP64 of International Protection Marking (IEC 60529).

15. The actuating and sensing module according to claim 1, wherein the first protective membrane and the second protective membrane comply with Rating IP65 of International Protection Marking (IEC 60529).

16. The actuating and sensing module according to claim 1, wherein the first protective membrane and the second protective membrane comply with Rating IP66 of International Protection Marking (IEC 60529).

17. The actuating and sensing module according to claim 1, wherein the first protective membrane and the second protective membrane comply with Rating IP67 of International Protection Marking (IEC 60529).

18. The actuating and sensing module according to claim 1, wherein the first protective membrane and the second protective membrane comply with Rating IP68 of International Protection Marking (IEC 60529).

19. An actuating and sensing module; comprising:
- at least one first substrate comprising at least one intake channel, at least one exhaust channel, at least one inlet and at least one outlet, wherein the at least one intake channel and the at least one exhaust channel are in communication with an outside of the at least one first substrate through the at least one inlet and the at least one outlet, respectively;
- at least one second substrate comprising at least one through slot, wherein the at least one through slot is disposed in its open setting;
- at least one valve membrane comprising at least one intake valve and at least one exhaust valve, wherein the at least one valve membrane is disposed between the at least one first substrate and the at least one second substrate, and the at least one intake valve and the at least one exhaust valve are configured to close and insulate the at least one intake channel and the at least one exhaust channel, respectively;
- at least one actuating device disposed in the at least one second substrate and covering the at least one through slot, so as to form at least one compressing chamber between the at least one valve membrane and the at least one through slot of the at least one second substrate, wherein the at least one inlet, the at least one intake channel, the at least one compressing chamber, the at least one exhaust channel and the at least one outlet are in communication with each other to form at least one gas flow loop; and at least one sensor disposed in the at least one gas flow loop;

wherein, while the at least one actuating device is enabled to drive the at least one intake valve of the at least one valve membrane to vibrate upwardly and be opened, a gas is inhaled from outside into the at least one intake channel through the at least one inlet of the at least one first substrate and transferred to the at least one compressing chamber through the at least one intake valve of the at least one valve membrane, wherein, while the at least one actuating device compresses the gas in the at least one compressing chamber and drives the at least one exhaust valve of the at least one valve membrane to vibrate downwardly and to be opened, the gas is transferred to the at least one exhaust channel and discharged out through the at least one outlet of the at least one first substrate, so that the gas circulated in the at least one gas flow loop is sensed by the at least one sensor, wherein the at least one first substrate further comprises at least one first protective membrane and at least one second protective membrane, wherein the at least one first protective membrane is disposed to cover the at least one inlet, the at least one second protective membrane is disposed to cover the at least one outlet, wherein the at least one first protective membrane and the at least one second protective membrane includes a waterproof, dustproof and gas-allowed film structure, respectively.

* * * * *